Figure 1:
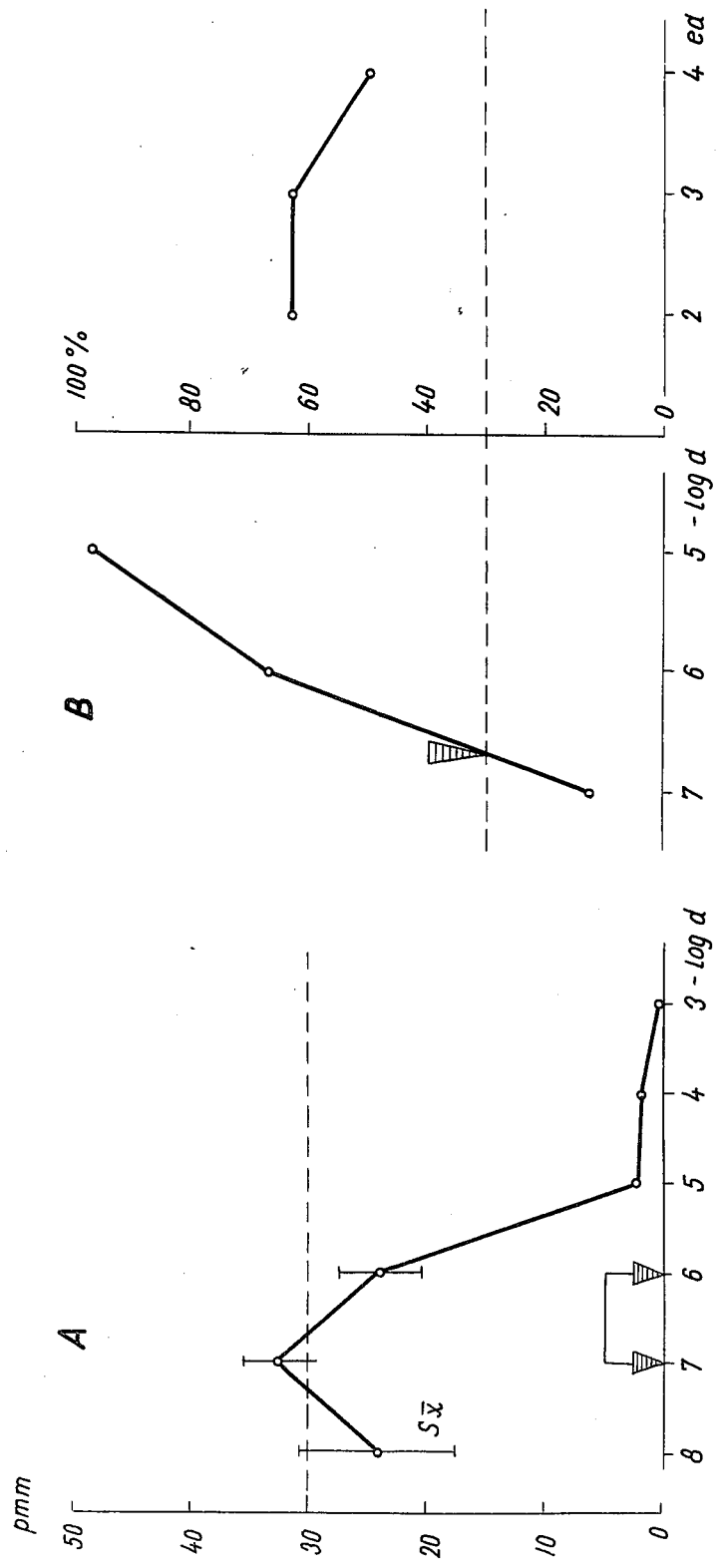

United States Patent [19]
Jelínek et al.

[11] 4,153,676
[45] May 8, 1979

[54] METHOD FOR TESTING OF EMBRYOTOXICITY ON CHICKEN EMBRYO

[75] Inventors: Richard Jelínek; Zdeněk Rychter; Miroslav Peterka, all of Prague, Czechoslovakia

[73] Assignee: Ceskoslovenska akademie ved, Prague, Czechoslovakia

[21] Appl. No.: 778,043

[22] Filed: Mar. 16, 1977

[30] Foreign Application Priority Data

Apr. 2, 1976 [CS] Czechoslovakia .................. 2170-76

[51] Int. Cl.² .................. A61K 29/00; G01N 33/00; G01N 33/08
[52] U.S. Cl. .................. 424/9; 195/1.7; 195/1.8; 424/3
[58] Field of Search .................. 424/3, 9; 195/1.7, 1.8

[56] References Cited
PUBLICATIONS

Jelinek, Folia Morphologica, vol. XIX (1971), pp. 60–137, photo, 2 pages.
Jelinek, Folia Morphologica, vol. XVIII (1970), pp. 125–137, photo, 2 pages.
Klika, Folia Morphologica, vol. XVII (1969), pp. 29–40, photo, 6 pages.

*Primary Examiner*—Anna P. Fagelson
*Attorney, Agent, or Firm*—Burgess, Ryan and Wayne

[57] ABSTRACT

Method for testing of the embryotoxicity in the chicken embryo consists in reading the response of caudal morphogenetic system (CMS) of a chicken embryo to the presence of the tested substance in subgerminal fluid. The function of the caudal morphogenetic system is evaluated 24 hours after application by a simple quantitative parameter — the length of a newly-formed part of the trunk. The substance, which interferes with some of the basic morphogenetic processes, slows down, stops or modifies the formation of the shape of the caudal part of trunk. Considering that the quantitative parameter is used as the index of the CMS function, each member of the experimental set presents information, not only the dead and malformed embryos as in classical methods. The second part of the test, i.e. the more precise determination of the beginning of the direct embryotoxicity range, serves above all for disclosure of the effect of the tested substance on the circulation system of the embryo and smooth muscles of faetal membranes. The testing according to this method may be used in pharmaceutical productions and plants, further in chemical productions and for environmental monitoring.

6 Claims, 3 Drawing Figures

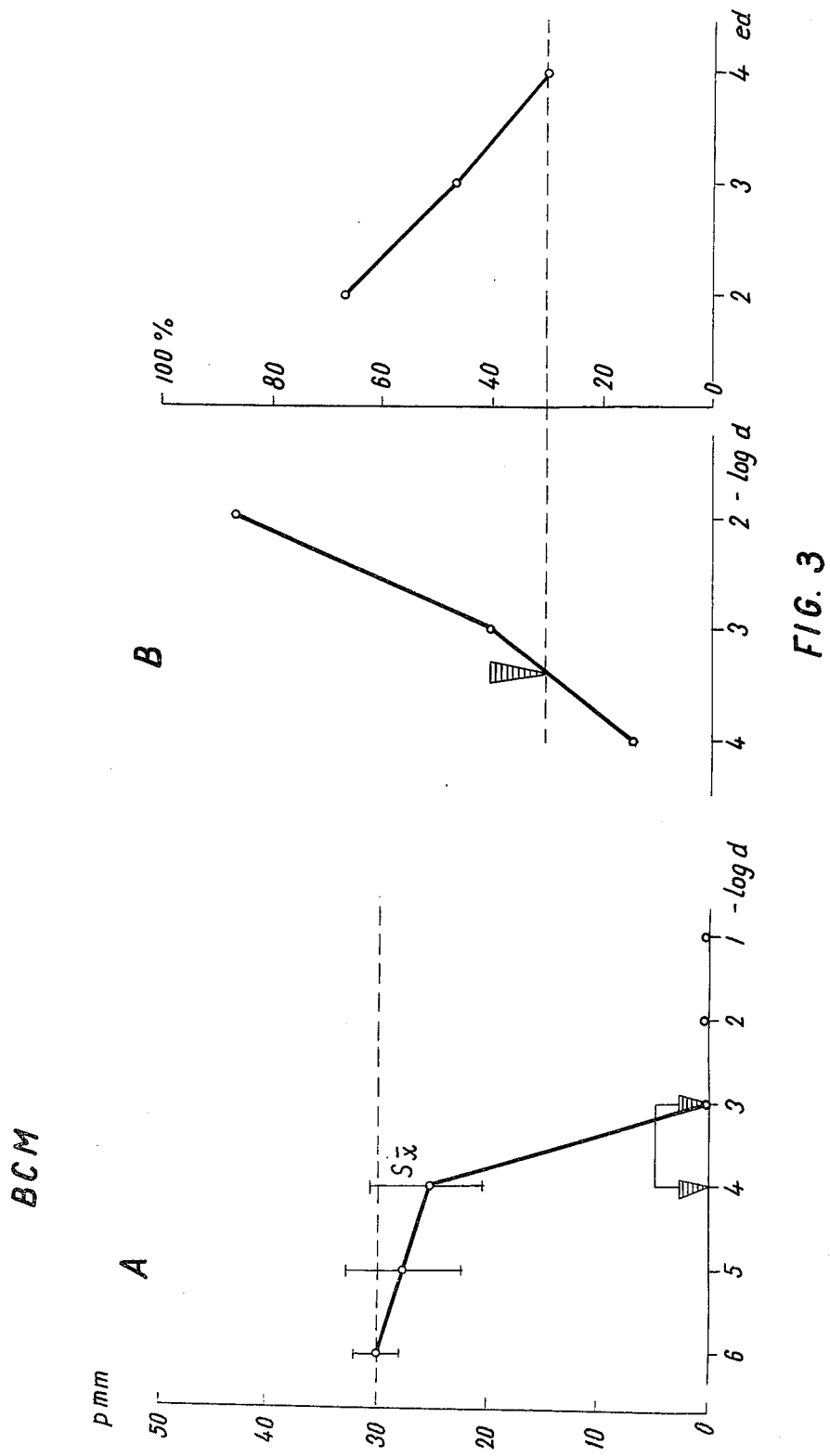

METHOD FOR TESTING OF EMBRYOTOXICITY ON CHICKEN EMBRYO

The invention relates to a method for the testing of embryotoxicity of a substance on a chicken embryo.

Testing of undesirable effects upon foetus development have become an integral part of toxicological safeguard of new drugs. Introducing a new drug to the market is legislatively bound in most countries to the performance of prescribed tests. Testing has been carried out, until now, according to regulations which were formulated in accord with recommendations of WHO (1967, 1975) based on the classical, substantially empirical approach. See, for example, Robson, J. M.: Testing drugs for teratogenicity and their effects on fertility; Brit. Med. Bull. 1970, 26 (212–216); Dyban, A. P., Baranov, V. S., Akimova, I. M.: The basic methodological approaches to testing the teratogenic activity of chemical substances; Arkh. Anat. Gistol Embriol. 1970, 59 (89–100); Tuchmann-Duplessis, H.: Teratogenic screening methods and their application to contraceptive products: Acta Endocrinol., Suppl. 185, 1974 (203–223). This approach consists in application of the tested drug via the maternal organism (i.e. administration to a pregnant female) of at least two species of testing animals and the results are evaluated according to the occurrence of dead and malformed foetuses. This method is lengthy and expensive and cannot easily be made shorter due to its empirical nature (Wilson, J. G.: Reproduction and teratogenesis—Current methods and suggested improvements; J. Assoc. Off. Anal. Chem. 1975, 58 (657–667).

The above disadvantages are overcome in the present method for testing of embryotoxicity on chicken embryos consisting in utilization of the quantitative response of the caudal morphogenetic system to estimate the embryotoxically effective dose range of the tested substance, which is then determined more precisely on the basis of the quantitative reaction of other morphogenetic systems after the substance has been applied to the immediate environs of embryo in the higher developmental stage. The lowest concentration of the tested substance which already affects the function of the caudal morphological system of the chicken is determined with two-day old chicken embryos of stage HH 10-11 (Hamburger V., Hamilton H. L.: J. Morph. 1951, 88 (49–92)) by measuring the length of the newly-formed part of the trunk after a further 24 hours of incubation. This value is then verified by counting the number of dead and malformed enbryos in the eighth day of incubation after a single application in the second, third and fourth day of embryo development. The beginning of the embryotoxic effect of the tested substance is eventually determined as the intersection of the curve showing dependence between the dose and effect under the above defined application conditions and the level of a non-specific response of embryos after application of the same volume of solvent of the tested substance as was the volume of the tested substance solution in this solvent. The lowest concentration of the tested substance which affects the function of the caudal morphological system of the chicken is ascertained by application of a dilution series of this substance in a solvent, where the concentration forms a decimal geometric series from $10^{-1}$ to $10^{-10}$ of the effective substance in the volume 3–10 ul., and this lowest concentration of substance is then used, together with the concentration lower and higher by one order of magnitude, for single application in the second, third and fourth day of embryo development. Disorders in the development of the cranial vault, facial region, extremities, abdominal wall, caudal end of trunk and malformations of heart which are detectable under a preparation microscope in the eighth day of incubation are evaluated as malformations. Distilled water, physiologic saline, aqueous ethanol up to 30%, aqueous dimethylsulfoxide up to 10%, and aqueous carboxymethylcellulose solution up to 1% were used as application media.

The present method of testing is based on recent knowledge concerning the relationship of embryonic morphogenetic systems of various species and classes, specificity of metabolic systems of the maternal organisms, and the transport of extraneous substances through the placental barrier (Boréus, L. O. (Ed.): Fetal Pharmacology, Raven Press, N.Y. 1973, p. 487).

The principle of the present method consists in reading the response of the caudal morphogenetic system (CMS) of the chicken embryo (st. HH 10-11) to the presence of the tested compound in the subgerminal fluid. The function of the caudal morphogenetic system is evaluated 24 hours after application by means of a simple quantitative parameter, i.e. the length of the newly-formed part of the trunk. The substance, which interferes with some of the basic morphogenetic processes, retards, stops or modifies the formation of the shape of the caudal part of the trunk. Considering that the quantitative parameter is used as an index of CMS function, each number of the experimental set renders the information and not only the dead and malformed embryos as in classical methods. The other part of the test, i.e. the more precise determination of the beginning of the embryotoxicity range, serves above all for disclosure of the effect of the tested substance on the circulation system of the embryo and the smooth muscles of foetal membranes.

The merits of the present procedure consist above all in the speed in obtaining results and in modest material and time requirements which allow to obtain the information about direct embryotoxicity of the substance, including its known metabolites, in a short time. The consumption of the test substance is minimal (mostly does not exceed 5 mg) so that such compounds may be tested which are available only in limited amounts for any reason.

The purpose of the proposed procedure is the rapid and precise determination of the minimum dose of the tested substance or other factor which significantly affects the morphogenesis of embryos. The testing according to this method can be employed in pharmaceutical plants and production, in chemical production and for environmental monitoring. The method is based on the theory of elementary morphogenetic processes and on the finding that the main factor of variability of the response to action of teratogenic impulse are not the different properties of the embryonal morphogenetic systems but the maternal organism.

The procedure for determination of the potential harmful effects to the development of the foetus used until the present time is essentially empirical and consists in exposure of the female experimental animal to the action of the examined factor during the complete period of pregnancy. At least two doses and two animal species are mostly used. The effect of the factor is read closely before litter and is evaluated from the number of malformed and dead foetuses.

The present procedure utilizes the technique of direct application of the substance into the immediate environs of the chicken embryo. The application tool is a glass micropipette with a bent, sharply ground tip (100 um in diameter) calibrated to 3, 10 and 100 ul. The pipette is freely connected to a polyethylene tube with mouthpiece and exchangable filter.

The testing procedure consists of three parts:

I. The estimation of direct embryotoxicity range

II. The more precise determination of the beginning of direct embryotoxicity range III. The estimation of embryotoxicity range of specific metabolites.

I. Estimation of direct embryotoxicity range—The chick embryotoxicity screening test—CHEST The tested substance is diluted with distilled water in a decimal geometric series starting with 1:100 dilution (5 mg/0.5 ml) to a concentration 1:1,000,000 and, if necessary, the pH is adjusted to obtain a final pH of the solution between 4 and 9. If the substance is insoluble in water, 30% ethanol, 10% dimethylsulfoxide or 1% carboxymethalcellulose can be used as the solvent. The series of increasing concentrations $10^{-6}$–$10^{-2}$ is obtained by injecting each solution with the above described micropipette in an amount of 3 ul into the subgerminal area of six chicken embryos, exclusively of HH 10-11 stages (stages according Hamberger and Hamilton, 1951, approximately 40 hours of incubation at 37.5° C.). The application is carried out under a preparation microscope, best at a magnification 10×. The eggs are opened with the usual window technique, after application and moistening of the blastoderm with a single drop of saline, are covered with glass on a paraffin frame and stored again in the incubator. The whole procedure requires semisterile conditions. After another 24 hours of incubation, the distance between arteriae vitallinae and the caudal pole of the trunk in each embryo is measured under the preparation microscope by means of an oculer micrometer in one of the eyepieces and the lengths thus obtained are plotted on a graph on the ordinate axis, while the logarithm of the dilution of the tested substance is plotted on the abcissa. The reading is facilitated by a short-term vital staining of the embryo with a drop of 0.5% solution of Neutral Red. The cases where the arteries were not developed are evaluated as a zero distance. In this way, 6 values are obtained for each concentration of the tested substance and the position of the median is laid out. By connection of the medians of the values of all concentrations, the curve is obtained which descends in the dependence on dose in the case when the tested substance is effective in the given dosage. The beginning of the embryotoxicity range is between the last ineffective concentration and the first statistically significant effective concentration which is followed by a monotonous decrease. The statistical significance is best evaluated by the rank test according to Wilcoxon for two independent selections (Z. Roth et al, Statisticke Metody v. Experimentalni Medicine, 1962, pg. 589). If the substance is already effective at a concentration $10^{-5}$ and lower, further series of concentrations in the region $10^{-4}$–$10^{-9}$, etc., is tested as far as the normal values are obtained (a curve parallel with the abcissa).

Data survey:
Consumption of the tested substance: 5 mg
Consumption of HH 10-11 embryos: as a rule 36
Time required for preparation: 1 hour
Time required for application: 1 hour
Time required for evaluation: 0.5 hour
The result is known 24 hours after application.

II. The more precise determination of the beginning of the direct embryotoxicity range consists in verification of the preceding estimate with higher developmental stages.

The last ineffective dose and the first two effective doses as determined in part I are applied singly to embryos incubated 2 (st. HH 11-14), 3 (st. HH 17-20), and 4 days (st. HH 21-24) under the same conditions. The solutions are injected in the second day subgerminally and, in the third and fourth day, intraamniotically, always to 10 embryos at the same day and dose (the total number is 90). The embryos after application are further incubated to the eighth day of the embryonal development and then they are withdrawn, weighed without embryonal membranes and evaluated under a preparation microscope in terms of malformations of the head (exencephaly, cranioschisis, cleft lip), extremities (reduction deformities occurrence of supernumerary structures), trunk (syndrome of caudal regression, defects of body wall) and, after cutting the body wall and right ventricle of the heart, also occurrence of heart malformations (transpositions, defects of interventricular septum). An interventricular septal defect occurring in embryos of higher weight than 1000 mg is evaluated as an abnormality. The dissection is performed with ophthalmological tools, in the best way in a dish cast with paraffin and filled with water, while the embryo is fixed in the supine position by entomologic pins. During evaluation of results, the number of dead and malformed foetuses is summed up in every group and plotted into the contingency table, the marginal sums (T) are made and arithmetic means ($\bar{x}$) are calculated. The latter multiplied by ten indicates the incident affection in percent:

| Day of application | 2nd | 3rd | 4th | $T_{+j}$ | $\bar{x}_{.j}$ |
|---|---|---|---|---|---|
| Dose | | | | | |
| $10^{n-1}$ | $x_{11}$ .. | | | | |
| $10^{n}$ | | | | | |
| $10^{n+1}$ | | | .... 33 | | |
| $T_{i+}$ | | | | | |
| $x_{i.}$ | | | | | |

The mean values of lines ($\bar{x}_j$) show the dependence of effect on the applied dose, the mean values of columns ($\bar{x}_i$) show the dependence on the day of application. The beginning of the embryotoxicity range lies in the range of doses where the incidence of affected (i.e. dead or malformed) foetuses exceeds the 30% level, which was ascertained with respect to the non-specific effect of intervention and the basal frequency of spontaneously occurring malformations.

Data survey:
Consumption of the tested substance: max. 5 mg
Consumption of applicable embryos: 90
Time required for preparation: 2 hours
Time required for application: 3 hours
Time required for evaluation: 3 hours
The result is known 6 days after application.

The testing result according to the present method may be approximated for a situation when the tested substance is applied via the maternal organism as it is usual with mammals. The beginning of the embryotoxicity region for the mammalian embryo may be approximately determined by multiplying the estimate obtained with the chicken embryo by the index $10^{-2}$.

Example:

The beginning of the embryotoxicity range determined by the CHEST method ranged between $10^{-4}$ and $10^{-3}$ concentration of the applied solution. The probable beginning of the embryotoxicity region for mammals can be calculated as follows:

$$(10^{-4} \text{ to } 10^{-3}) \times 10^{-2} = 10^{-6} \text{ to } 10^{-5},$$

i.e. 1-10 mg per kg of weight of a pregnant female.

The method is illustrated by the results of testing of three different substances presented in graphical form.

Figure 2:
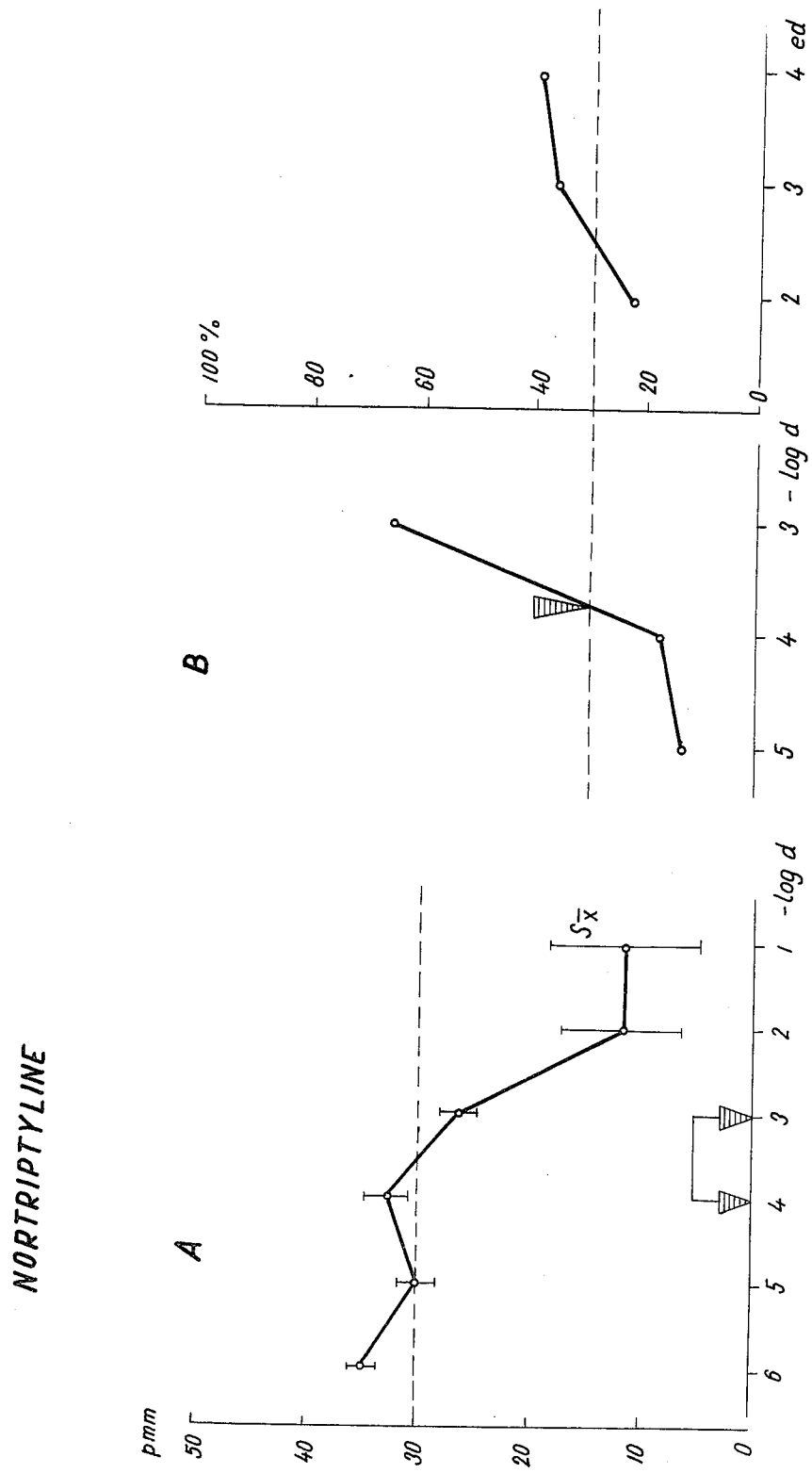

FIG. 1 shows the result of embryotoxicity testing of the known teratogen Actinomycin D (water was used as a solvent for injection); FIG. 2 includes results of embryotoxicity testing of the tricyclic antidepressant Nortriptyline (10% aqueous solution of dimethylsulfoxide was used as a vehicle); and FIG. 3 contains the result of the same testing of the pesticidal substance BCM—Carbendazim; methylbenzimidazole carbamate (1% aqueous solution of carboxymethylcellulose was used as a vehicle). Each of the given figures includes two plots —A and B. The result of an estimate of the direct embryotoxicity range is given in plots A; the axis of abscissas: log α-dilution of the substance in the applied solution; the axis of ordinates: the length of the newly-formed part of the trunk 24 hours after application in projection millimeters (pmm=mm×13). The curve connects mean values, the data scattering is expressed as a standard deviation of the mean $(s_{\bar{x}})$. The dashed horizontal line indicates the lower limit of the confidence interval of the average trunk length in reference embryos. The embryotoxicity range begins in the range of hatched arrows.

The plot B shows the more precise determination of direct embryotoxicity dose range. The dependence of effect on the dose is plotted on the left of axis of ordinates. The axis of abscissae: log α-dilution of the substance in the applied solution; the axis of ordinates: occurrence of dead and malformed foetuses in the eighth day of incubation after single application in the 2nd, 3rd and 4th day of embryonal development in percent. The dashed horizontal line: noise level (i.e. the spontaneous frequency of dead and malformed foetuses plus a non-specific effect of the experimental intervention). The beginning of direct embryotoxicity range of the tested substance is indicated by a hatched arrow. The dependence of effect on the day of application (ed) is shown on the right of axis of ordinates. The result found:

According to FIG. 1 relating to testing of Actinomycin D, the beginning of the embryotoxic effect in mammals may be assumed in the dose region of 0.001-0.01 mg per kg of mother weight.

According to FIG. 2, which relates to testing of Nortriptyline, the beginning of the embryotoxic effect in mammals may be assumed in the dose region of 1-10 mg per kg of mother weight. According to FIG. 3 showing the testing of BCM, this beginning is again in the dose region of 1-10 mg/kg of mother weight.

We claim:

1. A method for testing a substance for embryotoxicity comprising the steps of:
   (A) administering a solution of said substance to a plurality of two-day chicken embryos in graduated dosage levels;
   (B) measuring the quantitative response of the caudal morphogenetic system of said embryos to said substance by measuring the length of the newly-formed part of the trunks of the embryos after a 24 hour incubation period, verifying this value by
   (C) administering said substance in a single application to said further plurality of embryos in the second, third and fourth day of embryonal development and counting the number of dead and malformed embryos in the eighth day of incubation, plotting dependence between the dose and effect under the above given conditions of application, to form a curve, and
   (D) plotting the level of nonspecific effect on the embryo after application of the same volume of solvent for the tested substance as was the volume of the solution of the tested substance in this solvent, whereby the lowest embryotoxically effective dose of said substance is represented by the intersection of said curve with said level.

2. The method of claim 1, wherein the lowest concentration of said substance which already affects the function of the caudal morphogenetic system of the chicken is determined by application of a dilution series of the substance in a solvent representing the decimal geometric series of concentrations $10^{-1}$ to $10^{-10}$ of the effective substance in a volume 3-10 μl and this lowest concentration of substance is then applied together with the concentrations lower and higher by an order of magnitude, in the second, third and fourth day of embryonal development.

3. The method of claim 1, wherein defects in the development of the cranial vault, facial region, extremities, abdominal wall, caudal end of the trunk and malformations of the heart detectable under the preparation microscope are evaluated as malformations.

4. The method of claim 1, wherein distilled water, physiologic saline, an aqueous solution of ethanol up to 30%, an aqueous solution of dimethylsulfoxide up to 10%, or an aqueous solution of carboxymethylcellulose up to 1% are used as the solvent medium.

5. A rapid method for testing a substance for embryotoxicity which comprises:
   (A) administering said substance subgerminally to a plurality of chicken embryos in incubated eggs in the HH 10-11 stage, in graduated dosage levels;
   (B) incubating said plurality of eggs containing said composition to be tested for about 24 hours;
   (C) measuring the distance between the arteriae vitellinae and the caudal pole of the embryo;
   (D) comparing the distance between the arteriae vitellinae and caudal pole of the embryos in the eggs containing the substance to be tested with embryos in eggs not containing the substance to be tested whereby the lowest dose level which shortens the distance between the arteriae vitellinae and the caudal pole has an embryotoxic effect.

6. The method of claim 5 which further comprises:
   (A) administering a solution of said substance in the two lowest effective dose levels and highest ineffective dose level to a plurality of chicken embryos in incubated eggs in the HH 11-14, HH 17-20 and HH 21-24 stages wherein said dose of said substance is administered subgerminally to said HH 11-14 stage eggs and intramniotically to said HH 17-20 and HH 21-24 stage eggs;
(B) counting the number of dead and malformed embryos after the eighth day of incubation;
(C) plotting the dependence between the dose and effect under the above conditions to form a curve and plotting the level of non-specific effect on the embryo after application of the same volume of solvent for the tested substance as was the volume of the solution of the test substance in this solvent whereby the lowest embryotoxically effective dose of said substance is represented by the intersection of said curve with said level.

* * * * *

UNITED STATES PATENT OFFICE
CERTIFICATE OF CORRECTION

Patent No. 4,153,676  Dated May 8, 1979

Inventor(s) Richard Jelinek, et al

It is certified that error appears in the above-identified patent and that said Letters Patent are hereby corrected as shown below:

In the Abstract, line 5 from bottom: "faetal" should be
--foetal--.

Column 1, line 67  "ul." should be --µl.--.

Column 3, line 37:  "vitallinae" should be --vitellinae--.

Signed and Sealed this

Twentieth Day of November 1979

[SEAL]

Attest:

RUTH C. MASON
Attesting Officer

LUTRELLE F. PARKER
Acting Commissioner of Patents and Trademarks